United States Patent [19]

King, Jr. et al.

[11] Patent Number: 5,663,406

[45] Date of Patent: Sep. 2, 1997

[54] FORMATION OF CARBONATE ESTERS AND ORTHOCARBONATES

[75] Inventors: Joseph Anthony King, Jr.; Robert Edgar Colborn; Deborah Ann Haitko, all of Schenectady; Jimmy Lynn Webb, Ballston Lake, all of N.Y.

[73] Assignee: General Electric Company, Schenectady, N.Y.

[21] Appl. No.: 758,108

[22] Filed: Nov. 25, 1996

Related U.S. Application Data

[63] Continuation of Ser. No. 494,040, Jun. 26, 1995, abandoned.

[51] Int. Cl.$^6$ .................... C07C 68/00; C07C 68/06
[52] U.S. Cl. .................... 558/243; 558/274; 568/592
[58] Field of Search .................... 558/243, 274; 568/592

[56] References Cited

FOREIGN PATENT DOCUMENTS 230725  7/1909  Germany .

OTHER PUBLICATIONS

The Effect of Nitrogen Donors on the Reactivity of Copper (I) Aryloxides: Synthesis of Thioncarbonates. Narasimhamurthy, N. and A.G. Samuelson. Tetrahedron Letters, vol. 29, No. 7, 1988, pp. 827–830 (Great Britain).
Synthesis of Aryl Orthocarbonates. Narasimhamurthy, N. and A.G. Samuelson. Tetrahedron Letters, vol. 27, No. 8, 1986, pp.991–992 (Great Britain).
Hydrolysis of Orthocarbonates. Evidence for Charge Imbal.in the Transition State for the Gen. Acid Catalyzed Process. Kandanarachchi, Pramod and Michael L. Sinnott. J. of Am. Chem. Soc. 1994, 116, 5601–5606.
Destabilisations of a Carbocation by $\alpha$–Oxygen Substitution: the Hydrolysis of Othocarbonates. Kandanarachchi and Michael L. Sinnott. J.Chem. Soc., Chem Commun., 1992. pp. 777–778.

Hydrolysis of Aryl Orthocarbonates by General Acid Catalyzed and Spontaneous Process. Kandanarachchi and Michael L. Sinnott. J.Am. Chem. Soc. 1994, 116, 5592–5600, 5601–5606.

A Convenient Preparation of DI–n–Butyltin Diphenoxides. Rees, R.G. and A.F.Webb. Journal of Organometallic Chemistry, 12 (1968), pp. 239–240.

Organotin Chemistry. Considine, W.J. and J.J. Ventura, J. Org. Chem. 28(1963) 221.

Synthesis of Carboxylic and Carbonic Ortho Esters. Robert H. DeWolfe. Mar. 1974. Department of Chemistry, University of CA, Santa Barbara, CA. 93106.

Reatction of Dialkyltin Dialkoxides with Carbon Disulfide at Higher Temperature. Sakai, Shizuyoski, Yoshihiro Kobayashi, and Yoshio Ishit. J. Org. Chem., vol. 36, No. 9, 1971, pp.1176–1180.

Synthetic Utility of Copper (I) Phenoxide Complexes. Narasimhamurthy, N. and A.G. Samuelson, Proc. Indian natn. Sci. Acad., 55, A, No. 2, 1989, pp. 383–391.

*Primary Examiner*—Johann Richter
*Assistant Examiner*—Michael G. Ambrose
*Attorney, Agent, or Firm*—William H. Pittman

[57] ABSTRACT

A carbonate ester is produced by the metal-induced reaction of a hydroxy compound with a sulfur compound in a melt process. An orthocarbonate can also be produced. The orthocarbonate can be converted into carbonate ester in a subsequent operation.

20 Claims, No Drawings

FORMATION OF CARBONATE ESTERS AND ORTHOCARBONATES

This application is a continuation of application Ser. No. 08/494,040 filed Jun. 26, 1995, now abandoned.

BACKGROUND OF THE INVENTION

This invention relates to an inexpensive method to manufacture carbonate ester. More particularly, it relates to a method whereby carbonate ester is obtained by the metal induced reaction of a hydroxy compound with a sulfur compound.

Polycarbonate can be made by interfacial reaction or melt transesterification. The melt transesterification of a carbonate ester provides an environmental advantage over the reaction of hydroxy compounds, such as bisphenols, with phosgene under interfacial reaction conditions. In addition, polycarbonates prepared by melt transesterification have low levels of contaminants, such as sodium and halide ions. This makes these materials particularly suitable for use in optical applications, such as the manufacture of compact disks.

Because of the benefits, there is an interest in the manufacture of polycarbonates by melt transesterification of carbonate esters. However, before it can be extensively exploited on a commercial scale, a satisfactory manufacturing method for the carbonate ester must be developed.

The prior art includes three potential commercial routes for the preparation of carbonate ester: direct phosgenation of a phenol in an organic medium; a multi-step, low conversion melt transesterification of dialkyl carbonate with a phenol using a catalyst such as a titanium compound; and the direct carbonylation of a phenol requiring a catalyst, for example Pd, that is difficult to recycle.

The present invention further provides a method of producing orthocarbonate which can be converted into carbonate ester in a subsequent operation. Methods to produce orthocarbonate have been disclosed in the prior art. Typically, these methods required the use of organic halides with a base. Trace amounts of carbonate ester have also been generated. These prior art methods typically utilize a procedure with a number of incremental steps wherein a cuprous phenoxide species is presynthesized and then combined with carbon disulfide in an organic solvent.

SUMMARY OF THE INVENTION

The instant invention provides a method of producing carbonate ester comprising the step of mixing a. a hydroxy compound of the formula

R—OH, wherein R is selected from the group consisting of substituted and unsubstituted alkyl radicals, and substituted and unsubstituted aryl radicals;

b. a sulfur compound selected from the group consisting of the formulas

R'=C=S, 

and

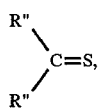

wherein R' is a divalent aliphatic radical, O or S, and R" is R or OR; and c. a promoter comprising at least one metal source that is capable of reacting with said hydroxy compound and said sulfur compound.

DESCRIPTION OF THE PREFERRED EMBODIMENTS

The instant invention relates to a method for manufacturing carbonate ester, which is subsequently used to produce polycarbonate. More particularly, it relates to a method whereby carbonate ester is obtained by the metal induced reaction of a hydroxy compound with a sulfur compound. Products of the present invention include, but are not limited to, diphenyl carbonate, di(O-phenyl) thiocarbonate, and diethyl carbonate.

The hydroxy compound comprises materials represented by the formula

R—OH, wherein R is selected from the group consisting of substituted and unsubstituted $C_{1-8}$ alkyl radicals, and substituted and unsubstituted $C_{6-13}$ aryl radicals. It includes cresols, bisphenol-A, xylenols, p-cumyl phenol, n-alkylated phenols, halogenated phenols, and alcohols. Preferably, the hydroxy compound includes either substituted or unsubstituted phenol, or anhydrous ethanol.

For use in the instant invention, the sulfur compound comprises materials represented by formulas selected from the following:

R'=C=S, 

and

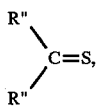

wherein R' is a divalent aliphatic radical, O or S; and R" is R or OR; and wherein R is as previously defined. These sulfur compounds can include carbon disulfide and di(O-phenyl) thiocarbonate.

There are many promoters known in the art that can be employed in the instant invention. Appropriate promoters comprise at least one metal source. The metal source must be capable of reacting with the organic species, particularly the hydroxy compound and the sulfur compound. It can include at least one mono- or polymetal oxide, alkyl metal oxide, metal halide or metal carboxylate. Metal oxides include oxides of metals selected from the group consisting of Fe, Ru, Os, Co, Rh, Ir, Ni, Pd, Pt, Cu, Ag, Au, Zn, Cd, Hg, In, Tl, Ge, Sn, Pb, Bi, Sb, Ti, and lanthanides. Appropriate metal oxides include, but are not limited to, $Cu_2O$, CuO, di-n-butyitin oxide, PbO, and $PbO_2$.

Where it is necessary to promote the solubility of the metal source so that it can react with the organic species, the promoter can also comprise a ligand. Such a ligand must be able to solubilize the metal source and still allow it to react with the organic species. The ligand can include any substituted mono-, bi-, or polydentate amines, imines, pyridines, quinolines, biquinolines, isoquinolines, terpyridines, phenanthrolines or nitriles. Ligands can include:

1,10-Phenanthroline
2,2'-Dipyridyl
2,2'-Dipyridylamine
2,2':6',2"-Terpyridine
N,N'-Di-t-butylethylene diamine Pyridine
4,7-Dimethyl-1,10-phenanthroline Acetonitrile The ligand may or may not be contained in the same molecule as the metal source. For example, di-n-butyltin oxide is both a metal source and a ligand, as it is sufficiently soluble without additional ligands.

Water may be added to the reagents. Water may be added in a quantity sufficient to render it a co-solvent with the hydroxy compound, such as phenol, wherein a homogeneously mixed solution results. Water can also be added in an excess quantity sufficient to produce a two phase system with the hydroxy compound.

The materials can reacted in either a batch or continuous process. They can be heated to a temperature of 20° C.–250° C. Preferably, they are heated to a temperature of 45°–180° C.

The reactor can be operated at reflux or under pressure. The pressure can range from atmospheric pressure to 20 MPa. Preferably, the pressure is held in the range of atmospheric pressure to 1 MPa. The reaction atmosphere can be comprised of air or an inert gas, such as argon or nitrogen. The reagents should be mixed sufficiently to generate a heterogeneous slurry.

The total reaction time is dependent in part on temperature and on the desired degree of completion of the reaction. The required reaction time is determinable by one skilled in the art.

Alternatively, orthocarbonate can be generated by the method of the instant invention. The orthocarbonate comprises materials represented by the formula:

wherein each R is as previously defined.

When orthocarbonate is generated, the method of the instant invention comprises a further step of converting the orthocarbonate to a carbonate ester. When the method is used to generate orthocarbonate as a precursor to carbonate ester, it is preferable to remove water formed during the reaction of the promoter, hydroxy compound and sulfur compound. This eliminates any potential hydrolysis during preparation of the orthocarbonate. This orthocarbonate can subsequently be used to produce a carbonate ester by acidic hydrolysis.

The materials produced by the present invention can be reacted under melt conditions with substantially no solvent present among the reagents. The process of the instant invention can also be run in the presence of a solvent. Suitable solvents are well known in the art. They include hydrocarbons such as toluene, xylenes, hexanes, heptanes, and octanes; acetonitrile; benzonitrile; ethers such as tetrahydrofuran, ether, dibutyl ether, and methyl butyl ether; methyl ethyl ketone; acetone; methyl isobutyl ketone; chlorinated hydrocarbons such as chlorobenzenes and dichlorobenzenes; nitromethane; and nitrobenzene.

All reagents can be used as received from the manufacturers. There is no need for pre-purification steps or drying steps prior to use of any of the reagents in the method of the instant invention.

The following examples are presented to enable those skilled in the art to understand more clearly and practice the present invention. These examples should not be considered as a limitation upon the scope of the present invention, but merely as being illustrative and representative thereof.

EXAMPLES

In each example described in the Table 1 and Table 2, the reagents were placed into a 125 ml glass Fischer Porter pressure vessel containing a stirstar. If the reaction atmosphere was to be air, the reactor vessel was then sealed. If the reaction atmosphere was to be argon gas, the reactor vessel was flushed three times with argon, pressurized with argon and then sealed. The sealed reactor vessel was then immersed in a preheated oil bath. The reagents were constantly stirred during the course of the reaction. The products of each reaction were analyzed by both liquid chromatography and gas chromatography and, in some cases, gas chromatography/mass spectrometry when it was appropriate.

Table 1 describes the results of the method of the instant invention when aromatic hydroxy compounds were used. In each of the examples of Table 1, the carbonate esters produced were diphenyl carbonate (DPC) and di(O-phenyl) thiocarbonate (PTC), while the orthocarbonate product was tetraphenoxy methane (TPM). All three products are considered useful relative to diphenyl carbonate production because the thiocarbonate and the tetraphenoxy methane can be subsequently converted to diphenyl carbonate. Table 2 describes the results when aliphatic hydroxy compounds were utilized in the method of the invention. In Table 2, the carbonate ester products were diethyl carbonate (DEC) and di(O-ethyl) thiocarbonate (ETC), while the orthocarbonate that was produced was tetraethoxy methane (TEM). Both tables indicate that a variety of metal sources, ligands, hydroxy compounds and sulfur compounds can be used to produce either a carbonate ester or an orthocarbonate.

When evaluating the effectiveness of each example, it is necessary to include both the quantity of carbonate ester produced and the quantity of orthocarbonate produced to determine the total product of the reaction. The ratio of PTC to TPM in the product is determined in part by the choice of the metal Source and the ligands around the metal. The ratio of TPM to DPC is a function of the temperature, the availability of water and the Lewis acidity of the metal source. A higher temperature promotes the production of more DPC. In Example 2, which was run at a temperature of 180° C., no TPM was detected in the product while Example 4, with the same reagents but a lower temperature of 80° C., generated more TPM than DPC. More water among the reagents also encourages the production of DPC. A greater Lewis acidity of the metal source also promotes the production of DPC. For this reason, the Cu(II) systems in the following examples generated more DPC than the Cu(I) systems. However, the Cu(I) systems, in general, produced more overall product than the Cu(II) systems. The yield on Example 6, with Cu(II), was lower than that of Example 13, which contained Cu(I).

It should be noted that in Examples 8–12, 14, and 15 the total product could have been doubled. Two atoms of Cu were available from each molecule of Cu$_2$O. An insufficient quantity of CS$_2$ was added to completely react all of the Cu available.

Examples 24 and 25 indicated the importance of dissolving the metal source in the melt. Tin can be a metal source when it can be adequately solubilized, such as when it is contained in di-n-butyltin oxide, Examples 16–18. However, in Examples 24 and 25, tin could not be solubilized effectively as SnO and $SnO_2$, resulting in no production of diphenyl carbonate or tetraphenoxy methane. The yield of Example 16 was lower than that of the Examples containing copper because of the different metal source. The activation of di-n-butyltin oxide is not as simple as the copper oxides.

PbO, in Examples 22 and 23, exhibited similar characteristics to tin. It should be noted that the oxide itself showed activity for the Pb.

Example 29 indicated that, more than one metal source can be incorporated into the mix.

Examples 31–33 showed that aliphatic hydroxy compounds were capable of producing product. The difference in the amount of product between Example 31 and 32 was probably attributable to the ratio of the metal source to carbon disulfide and ethanol.

TABLE 1

| Ex. No. | Metal Source | Qty (g) | Ligand | Qty (g) | Hydroxy Compound | Qty (g) | Sulfur Comp'nd | Qty (g) | Atm | psig | °C. | Hr |
|---|---|---|---|---|---|---|---|---|---|---|---|---|
| 1 | CuO | 6.689 | Bipy | 0.132 | phenol | 33.226 | $CS_2$ | 3.041 | Ar | 39 | 75 | 86. |
| 2 | CuO | 6.610 | Bipy | 0.125 | phenol | 23.127 | $CS_2$ | 3.065 | Ar | 38 | 130 | 18.5 |
| 3 | CuO | 6.463 | DPA | 0.137 | phenol | 22.826 | $CS_2$ | 3.051 | Ar | 32 | 128 | 18.5 |
| 4 | CuO | 6.364 | Bipy | 0.137 | phenol | 23.89 | $CS_2$ | 3.040 | Ar | 40 | 80 | 36. |
| 5 | CuO | 7.013 | TMEDA | 0.093 | phenol | 23.140 | $CS_2$ | 3.046 | Ar | 40 | 75 | 67. |
| 6 | CuO | 6.329 | Bipy | 0.125 | phenol | 25.227 | $CS_2$ | 3.041 | air | 36 | 42 | 95 |
| 7 | $Cu_2O$ | 5.724 | DPA | 0.0685 | phenol | 23.37 | $CS_2$ | 1.521 | Ar | 41 | 80 | 32. |
| 8 | $Cu_2O$ | 6.016 | Terpy | 0.095 | phenol | 20.301 | $CS_2$ | 3.125 | Ar | 42 | 130 | 18.5 |
| 9 | $Cu_2O$ | 5.908 | DBED | 0.067 | phenol | 21.070 | $CS_2$ | 3.046 | Ar | 23 | 130 | 18.5 |
| 10 | $Cu_2O$ | 5.752 | DPA | 0.0685 | phenol | 20.43 | $CS_2$ | 3.046 | | Atm | 132 | 16.5 |
| 11 | $Cu_2$) | 5.770 | Pyrd | 0.0633 | phenol | 19.85 | $CS_2$ | 3.046 | Ar | 35 | 80 | 52. |
| 12 | $Cu_2O$ | 5.887 | Bipy | 0.0685 | phenol | 19.877 | $CS_2$ | 3.046 | Ar | 40 | 80 | 52 |
| 13 | $Cu_2O$ | 6.034 | DPA | 0.0685 | phenol | 24.861 | $CS_2$ | 1.521 | Ar | 29 | 44 | 95 |
| 14 | $Cu_2O$ | 5.830 | DMphen | 0.0833 | phenol | 20.998 | $CS_2$ | 3.046 | | Atm | 131 | 17 |
| 15 | $Cu_2O$ | 5.836 | DMphen | 0.0083 | phenol | 21.385 | $CS_2$ | 3.046 | | Atm | 131 | 17 |
| 16 | DBTO | 40.06 | | | phenol | 60.0 | $CS_2$ | 6.089 | Ar | 40 | 65 | 45 |
| 17 | DBTO | 0.3243 | | | phenol | 21.616 | T-DPC | 0.285 | Ar | 32 | 85 | 16.5 |
| 18 | DBTO | 1.294 | | | phenol | 30.056 | T-DPC | 0.508 | Ar | 38 | 65 | 45 |
| 19 | DBTO | 0.540 | | | phenol | 20.75 | T-DPC | 0.520 | Ar | 36 | 90 | 13.75 |
| 20 | DBTO | 1.212 | | | phenol | 19.768 | T-DPC | 0.552 | Ar | 35 | 90 | 13.75 |
| 21 | DBTO | 0.580 | | | phenol | 19.746 | T-DPC | 0.512 | Ar | 38 | 90 | 66 |
| 22 | PbO | 2.232 | Bipy | 0.036 | phenol | 31.005 | $CS_2$ | 0.7614 | Ar | 42 | 90 | 16.5 |
| 23 | PbO | 0.4846 | Bipy | 0.034 | phenol | 32.059 | T-DPC | 0.500 | Ar | 40 | 85 | 16.5 |
| 24 | SnO | 11.027 | Bipy | 0.014 | phenol | 56.20 | $CS_2$ | 3.156 | Ar | 42 | 90 | 15 |
| 25 | $SnO_2$ | 6.061 | Bipy | 0.013 | phenol | 30.035 | $CS_2$ | 3.084 | Ar | 40 | 96 | 15 |
| 28 | | | | | phenol | 25.34 | T-DPC | 0.510 | Ar | 39 | 90 | 21 |
| 29 | CuO DBTO | 0.107 19.914 | Bipy | 0.125 | phenol | 29.44 | $CS_2$ | 3.041 | Ar | 35 | 104 | 22.5 |

| Ex. No. | DPC Qty (g) | DPC % yield | TPM Qty (g) | TPM % yield | PTC Qty (g) | PTC % yield |
|---|---|---|---|---|---|---|
| 1 | 1.131 | 13.2 | 4.614 | 30.0 | 0.111 | 1.2 |
| 2 | 3.505 | 40.91 | ND | ND | 0.070 | 0.76 |
| 3 | 3.11 | 36.3 | 0.0093 | 0.06 | 0.071 | 0.77 |
| 4 | 0.4057 | 4.73 | 4.878 | 31.72 | 0.0139 | 0.15 |
| 5 | 0.323 | 3.77 | 3.394 | 22.07 | 0.286 | 0.31 |
| 6 | 0.025 | 0.29 | 0.652 | 4.2 | 0.260 | 2.9 |
| 7 | 0.0458 | 1.1 | 2.020 | 26.3 | 0.161 | 3.5 |
| 8 | 0.561 | 6.5ª | 0.787 | 5.12 | 0.132 | 1.44 |
| 9 | 1.597 | 18.6ª | 0.205 | 1.33 | 0.0349 | 0.38 |
| 10 | 0.275 | 3.2ª | 0.860 | 5.6 | 0.0175 | 0.2 |
| 11 | 0.124 | 1.45ª | 0.607 | 3.95 | ND | ND |
| 12 | 0.223 | 2.6ª | 2.54 | 16.5 | 0.415 | 4.5 |
| 13 | 0.043 | 1.0 | 2.44 | 31.75 | 0.0517 | 1.1 |
| 14 | 0.269 | 3.1ª | 0.5537 | 3.6 | 0.611 | 6.63 |
| 15 | 0.547 | 6.38ª | ND | ND | 0.0127 | 0.14 |
| 16 | 0.586 | 3.42 | 0.0642 | 0.21 | 1.677 | 9.11 |
| 17 | 0.2089 | 78.81 | 0.0031 | 0.66 | 0.0469 | 20.53* |
| 18 | 0.3349 | 70.86 | 0.0497 | 5.857 | 0.1183 | 23.28* |
| 19 | 0.1588 | 32.8 | ND | ND | 0.349 | 67.2* |
| 20 | 0.122 | 23.76 | ND | ND | 0.421 | 76.24* |
| 21 | 0.1539 | 29.68 | 0.0853 | 9.98 | 0.1826 | 35.66* |
| 22 | 0.056 | 2.60 | 0.0145 | 0.377 | 0.0973 | 0.79 |
| 23 | 0.11 | 23.63 | 0.103 | 12.35 | 0.32 | 64.0* |
| 24 | ND | ND | ND | ND | ND | ND |
| 25 | ND | ND | ND | ND | ND | ND |
| 28 | ND | ND | ND | ND | 0.510 | 100.* |
| 29 | 3.00 | 17.45 | 0.0634 | 0.21 | 11.23 | 60.9 |

TABLE 2

| Ex. No. | Metal Source | Qty (g) | Ligand | Qty (g) | Hydroxy Compound | Qty (g) | Sulfur Comp'nd | Qty (g) | Atm | psig | °C. | Hr |
|---|---|---|---|---|---|---|---|---|---|---|---|---|
| 31 | CuO | 6.402 | Bipy | 0.150 | anhydrous ethanol | 31.172 | $CS_2$ | 3.041 | Ar | 35 | 105 | 23.5 |
| 32 | CuO | 11.446 | Bipy | 0.125 | anhydrous ethanol | 22.016 | $CS_2$ | 1.521 | Ar | 39 | 104 | 22 |
| 33 | $Cu_2O$ DBTO | 0.263 9.956 | Bipy | 0.152 | anhydrous ethanol | 21.681 | $CS_2$ | 1.521 | Ar | 40 | 106 | 22 |

| Ex. No. | DPC Qty (g) | DPC % yield | TPM Qty (g) | TPM % yield | PTC Qty (g) | PTC % yield |
|---|---|---|---|---|---|---|
| 31 |  | <0.5 | ND | ND |  | <0.5 |
| 32 | 0.025 | 0.7 | trace | <0.01 | 0.05 | 1.2 |
| 33 | 0.04 | 1.3 | trace | <1.0 | 0.06 | 0.9 |

ND — none detected
*recovered initial starting material
a — 50 mol % Cu available
DBTO Di-n-Butyltin Oxide
Phen 1,10-Phenanthroline
Bipy 2,2'-Dipyridyl
DPA 2,2'-Dipyridylamine
Terpy 2,2',6',2"-Terpyridine
DBED N,N'-Di-t-butylethylene diamine
Pyrd Pyridine
TMEDA N,N,N',N'-tetraethylethylene diamine
DMphen 4,7-Dimethyl-1,10-phenanthroline
DPC Diphenyl carbonate
TPM Tetraphenoxy methane
PTC Di(O-phenyl) thiocarbonate
Ar Argon
DEC Diethyl carbonate
TEM Tetraethoxy methane
ETC Di(O-ethyl) thiocarbonate

What is claimed is:

1. A method of producing carbonate ester comprising the step of preparing and reacting a mixture consisting essentially of
   (a) a hydroxy compound of the formula

R—OH, wherein R is selected from the group consisting of substituted and unsubstituted aryl radicals;
   (b) a sulfur compound selected from the group consisting of carbon disulfide and di-(O-phenyl) thiocarbonate;
   (c) a promoter comprising at least one metal source that is capable of reacting with said hydroxy compound and said sulfur compound; and, optionally,
   a ligand, water and a solvent.

2. A method in accordance with claim 1, wherein said promoter comprises at least one material selected from the group consisting of monometal oxides, polymetal oxides, alkyl metal oxides, metal halides and metal carboxylates.

3. A method in accordance with claim 1, wherein said promoter comprises at least one oxide of a metal selected from the group consisting of Fe, Ru, Os, Co, Rh, Ir, Ni, Pd, Pt, Cu, Ag, Au, Zn, Cd, Hg, In, Tl, Ge, Sn, Pb, Bi, Sb, Ti, and lanthanides.

4. A method in accordance with claim 1, wherein said promoter comprises at least one material selected from the group consisting of $Cu_2O$ CuO, di-n-butyltin oxide, PbO, and $PbO_2$.

5. A method in accordance with claim 1, wherein said promoter further comprises a ligand.

6. A method in accordance with claim 5, wherein said ligand is selected from the group consisting of monodentate amines, bidentate amines, polydentate amines, imines, pyridines, quinolines, biquinolines, isoquinolines, terpyridines, phenanthrolines and nitriles.

7. A method in accordance with claim 5, wherein said ligand is selected from the group consisting of 1,10-phenanthroline, 2,2'-dipyridyl, 2,2'-dipyridylamine, 2,2':6',2"-terpyridine, n,n'-di-t-butylethylene diamine, pyridine, 4,7-dimethyl-1,10-phenanthroline and acetonitrile.

8. A method in accordance with claim 5, wherein said ligand is chemically bonded to the metal source.

9. A method in accordance with claim 1, wherein said hydroxy compound is selected from the group consisting of unsubstituted phenols, cresols, bisphenol A, xylenols, p-cumyl phenol, n-alkylated phenols and halogenated phenols.

10. A method in accordance with claim 1, wherein said hydroxy compound is phenol.

11. A method in accordance with claim 1, further comprising the step of mixing water with said promoter, hydroxy compound and sulfur compound.

12. A method in accordance with claim 1, which is performed at a temperature of 20° C. to 250° C.

13. A method in accordance with claim 1, which is performed at a temperature of 45° C. to 180° C.

14. A method in accordance with claim 1, which is performed at a pressure of atmospheric pressure to 20 MPa.

15. A method in accordance with claim 1, which is performed at a pressure of atmospheric pressure to 1 MPa.

16. A method in accordance with claim 1, which is performed in an environment selected from the group consisting of air and inert gas.

17. A method in accordance with claim 1, which is produced an orthocarbonate the method and further comprises the step of converting said orthocarbonate to carbonate ester.

18. A method in accordance with claim 17, further comprising the step of removing water concurrently with orthocarbonate formation.

19. A method in accordance with claim 1, which is performed under melt conditions.

20. A method in accordance with claim 1, which is performed in the presence of a solvent and wherein said solvent is selected from the group consisting of hydrocarbons, acetonitrile, benzonitrile, ethers, methyl ethyl ketone, acetone, methyl isobutyl ketone, chlorinated hydrocarbons, nitromethane, and nitrobenzene.

* * * * *